US011337662B2

(12) United States Patent
Varlet et al.

(10) Patent No.: US 11,337,662 B2
(45) Date of Patent: May 24, 2022

(54) EXTRA ORAL DENTAL IMAGING APPARATUS WITH PATIENT POSITIONING ACCESSORY DETECTION

(71) Applicant: TROPHY, Croissy-Beaubourg (FR)

(72) Inventors: Stephane Varlet, Paris (FR); Olivier Nesme, Nogent-sur-Marne (FR); Yann Lecuyer, Paris (FR)

(*) Notice: Subject to any disclaimer, the term of this patent is extended or adjusted under 35 U.S.C. 154(b) by 0 days.

(21) Appl. No.: 16/627,008

(22) PCT Filed: Jun. 30, 2017

(86) PCT No.: PCT/IB2017/001002
§ 371 (c)(1),
(2) Date: Dec. 27, 2019

(87) PCT Pub. No.: WO2019/002903
PCT Pub. Date: Jan. 3, 2019

(65) Prior Publication Data
US 2020/0222014 A1    Jul. 16, 2020

(51) Int. Cl.
*A61B 6/14* (2006.01)
*A61B 6/04* (2006.01)
*A61B 6/00* (2006.01)

(52) U.S. Cl.
CPC .............. *A61B 6/14* (2013.01); *A61B 6/0421* (2013.01); *A61B 6/0492* (2013.01); *A61B 6/4452* (2013.01); *A61B 6/4494* (2013.01)

(58) Field of Classification Search
CPC ....... A61B 6/14; A61B 6/0421; A61B 6/0492; A61B 6/4452; A61B 6/4494; A61B 6/04
See application file for complete search history.

(56) References Cited

U.S. PATENT DOCUMENTS

| 6,118,842 | A  | * | 9/2000  | Arai ........................ A61B 6/032 378/38 |
| 10,376,434 | B2 | * | 8/2019  | Andersson ........... A61G 7/1065 |
| 2008/0230608 | A1 | * | 9/2008  | Lallemang ........... A61B 6/4494 235/439 |
| 2011/0299663 | A1 | * | 12/2011 | Steward, Jr. ......... G03B 42/042 378/170 |
| 2013/0071809 | A1 | * | 3/2013  | Kirkpatrick .............. A61B 6/14 433/29 |
| 2018/0263579 | A1 | * | 9/2018  | Lecuyer ............... A61B 6/0492 |

* cited by examiner

*Primary Examiner* — Marcus H Taningco

(57) ABSTRACT

Certain exemplary method and/or apparatus embodiments herein can include—a support frame, —a movable gantry that supports an x-ray source and an x-ray sensor in correspondence with the x-ray source and that is movable relative to the support frame, —a patient positioning accessory support member configured to support a patient positioning accessory of a specific type that is adapted to be used in the apparatus for conducting a specific examination on a patient, where the patient positioning accessory comprises at least one passive identification element that identifies the specific type of the patient positioning accessory, and the apparatus further comprises an active identification system that is configured to cooperate with the at least one passive identification element of the patient positioning accessory in order to identify the specific type of the patient positioning accessory.

16 Claims, 10 Drawing Sheets

EXTRA ORAL DENTAL IMAGING APPARATUS WITH PATIENT POSITIONING ACCESSORY DETECTION

TECHNICAL FIELD

The disclosure relates generally to the field of extra-oral dental x-ray imaging. More specifically, the disclosure relates to an extra oral dental imaging apparatus for obtaining a radiographic image of a patient.

BACKGROUND

A conventional extra oral dental x-ray imaging apparatus generally comprises: a support frame, a movable gantry that supports an x-ray source and an x-ray sensor in correspondence with the x-ray source and that is movable relative to the support frame.

Such an apparatus also comprises a patient positioning accessory support member that is configured to support a plurality of patient positioning accessories. Patient positioning accessories are used for positioning the anatomical structures of the head of a patient according to different orientations and for immobilizing the patient's head during an examination so as to reduce any possible movement.

One or several positioning accessories may be available for each type of examination (panoramic examination, 2D, 3D, 3D facial scanner etc.).

While such apparatuses may have achieved certain degrees of success in their particular applications, there is a need to ensure that a patient positioning accessory that is supported by the patient positioning accessory support member is appropriate with regard to the examination to be carried out by the physician.

SUMMARY

An object of the present disclosure is to identify a patient positioning accessory.

Another object of the present disclosure is to ensure that a patient positioning accessory is appropriate with regard to an examination to be carried out by the physician.

Certain exemplary method and/or apparatus embodiments of the application can ensure that a patient positioning accessory that is supported by the patient positioning accessory support member is appropriate with regard to the examination to be carried out by the physician.

These objects are given only by way of illustrative example, and such objects may be exemplary of one or more embodiments of the invention. Other desirable objectives and advantages inherently achieved by the may occur or become apparent to those skilled in the art. The invention is defined by the appended claims.

According to one aspect of the disclosure, there is provided an extra oral dental imaging apparatus for obtaining a radiographic image of a patient, the apparatus comprising a support frame, a movable gantry that supports an x-ray source and an x-ray sensor in correspondence with the x-ray source and that is movable relative to the support frame, a patient positioning accessory support member configured to support a patient positioning accessory of a specific type that is adapted to be used in the apparatus for conducting a specific examination on a patient, where the patient positioning accessory comprises at least one passive identification element that identifies the specific type of the patient positioning accessory, and the apparatus further comprises an active identification system that is configured to cooperate with the at least one passive identification element of the patient positioning accessory in order to identify the specific type of the patient positioning accessory.

Additional exemplary method and/or apparatus embodiments of the application can provide other possible features:
the apparatus further comprises an information system configured to generate information in relation with the specific type of the patient positioning accessory that has been identified.
the information system comprises a display assembly configured to display information in relation with the specific type of the patient positioning accessory that has been identified.
the apparatus is further configured to generate a visual indicator on the display assembly or on the patient positioning accessory, the visual indicator being in relation with the specific type of the patient positioning accessory that has been identified.
the active identification system is in the patient positioning accessory support member.
the patient positioning accessory support member is a patient positioning arm connected to the support frame.
the active identification system comprises:
one or several detection elements that are configured to cooperate with the at least one passive identification element of the patient positioning accessory and generate at least one signal depending on the result of the cooperation, and
a microprocessor configured to analyze the at least one signal thus generated in order to identify the specific type of the patient positioning accessory.
the active identification system is configured to mechanically or electromagnetically cooperate with the at least one passive identification element of the patient positioning accessory.
the one or several detection elements are selected among magnetic sensors, optical sensors, optical readers, at least one local position indicator, etc.
the at least one passive identification element of the patient positioning accessory is selected among a magnet, a mark or hole in the patient positioning accessory, an optical code on the patient positioning accessory, an RFID tag, a concavity in the outline of the patient positioning accessory, etc.

According to another aspect of the disclosure, there is provided an exemplary method for using an extra oral dental imaging apparatus for obtaining a radiographic image of a patient, the apparatus comprising:
a support frame,
a movable gantry that supports an x-ray source and an x-ray sensor in correspondence with the x-ray source and that is movable relative to the support frame,
a patient positioning accessory support member configured to support a patient positioning accessory of a specific type that is adapted to be used in the apparatus for conducting a specific examination on a patient,
wherein the method comprises:
installing the patient positioning accessory of a specific type on the patient positioning accessory support member,
identifying the specific type of the patient positioning accessory based on at least one passive identification element included in the patient positioning accessory.

According to a possible feature, the apparatus further comprises an active identification system and the method comprises causing cooperation between the active identification system and the at least one passive identification element of the patient positioning accessory in order to identify the specific type of the patient positioning accessory.

BRIEF DESCRIPTION OF THE DRAWINGS

The foregoing and other objects, features, and advantages of the invention will be apparent from the following more particular description of the embodiments of the invention, as illustrated in the accompanying drawings.
The elements of the drawings are not necessarily to scale relative to each other.

DETAILED OF EXEMPLARY EMBODIMENTS

Figure 1:
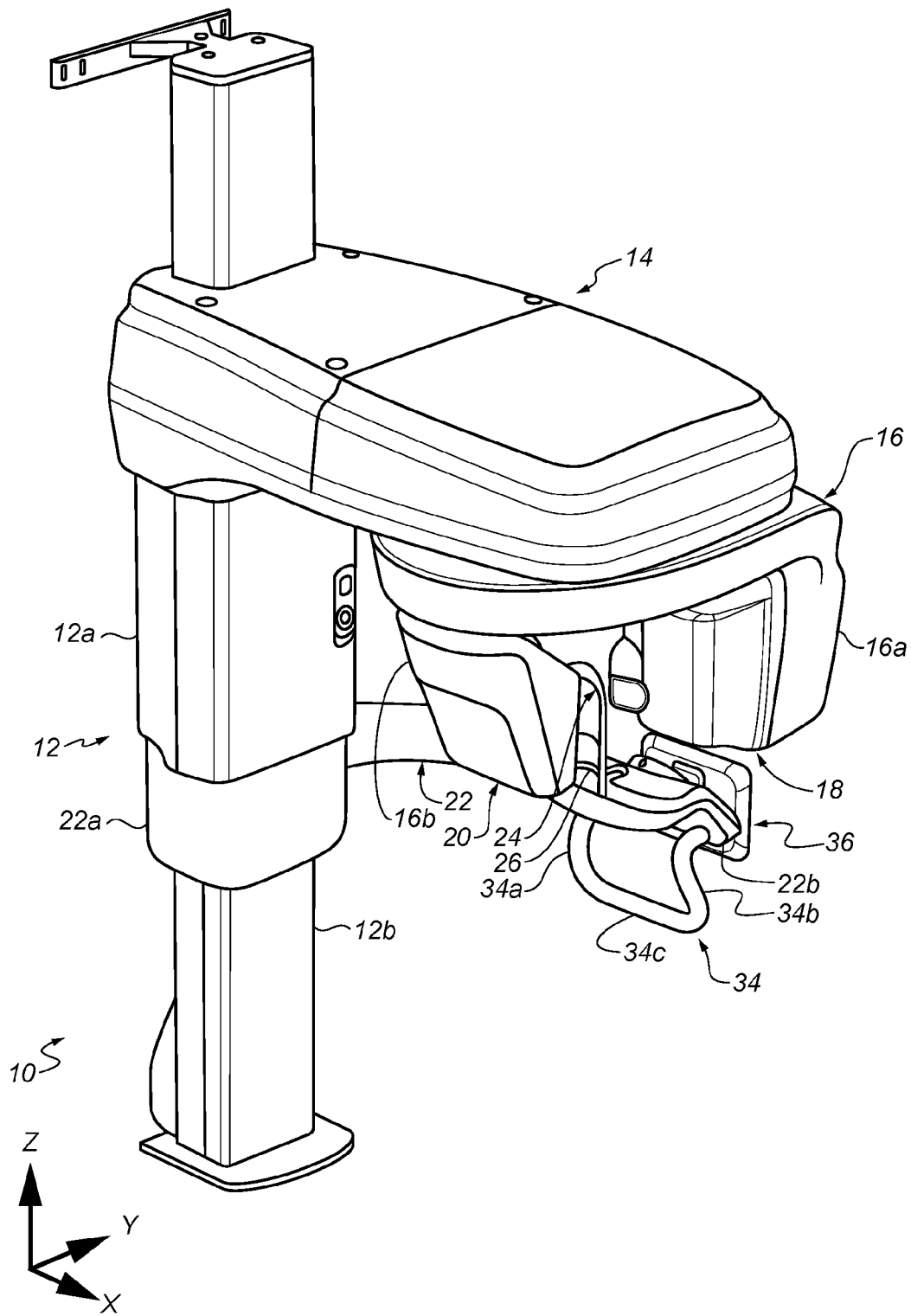
FIG. 1 shows an overall schematic perspective view of an extra-oral imaging apparatus according to an embodiment of the invention.

The following is a description of exemplary method and/or apparatus embodiments of the application, reference being made to the drawings in which the same reference numerals identify the same elements of structure in each of the several figures.

FIG. 1 illustrates an exemplary embodiment of an extra-oral imaging apparatus 10. Apparatus 10 comprises a support structure that includes a support frame 12 which may be a support column.

The support structure also includes a horizontal mount 14 that may be supported or held by the vertical column 12. Horizontal mount 14 extends away from vertical column 12 and may be substantially perpendicular thereto. Horizontal mount 14 can move vertically relative to the vertical column 12. More particularly, horizontal mount 14 is fixedly mounted on a vertical part 12a that is movably or slidably mounted over a fixed vertical part 12b. For example, an actuator, e.g. of the electric type, located behind the vertical column (not represented in the drawing) can be commanded to drive the horizontal mount 14 into a vertical movement in a controlled manner.

Horizontal mount 14 can support a gantry 16. Gantry 16 is movable relative to the support structure, and more particularly to horizontal mount 14. Gantry 16 may more particularly be rotatable relative to horizontal mount 14. Gantry 16 may be rotatable about a vertical axis of rotation which may be still during the operation of the imaging process or may follow one among several predetermined trajectories in accordance with the selected imaging process.

A driving known mechanism (not represented in the drawing) for driving the gantry 16 into a given movement is integrated inside horizontal mount 14. By way of example, such driving mechanism includes motors for imparting a first movement in a X, Y plane (e.g., X plane, Y plane, X and Y plane), e.g. two step by step motors, and a motor for imparting a rotational movement (e.g., about the vertical axis Z), e.g. a brushless motor.

Gantry 16 supports both an x-ray source 18 and at least one x-ray sensor 20 that is arranged in correspondence with the x-ray source. X-ray source 18 and the at least one x-ray sensor 20 may be arranged facing each other. Gantry 16 may include two opposite downwardly extending arms: a first arm 16a supports x-ray source 18 that is attached thereto and a second opposite arm 16b supports the at least one x-ray sensor 20 that is attached thereto.

When activated x-ray source 18 emits an x-ray beam, which here can radiate an imaging area of the patient's maxillofacial region, before impinging the at least one x-ray sensor 20.

In the present exemplary embodiment, the at least one x-ray sensor 20 may include a panoramic sensor, e.g. a slit-shaped sensor, a volumetric or computerized sensor (e.g. rectangular, square-shaped) or a cephalometric sensor or several sensors of one or several of the previous types.

Depending on the sensor or sensors present in the apparatus, one or several operating modes or imaging processes (1, 2 or 3) may be used among the projection, panoramic, volumetric or computerized tomography and cephalometric modes.

The support structure may also include a patient positioning accessory support member 22 which here is an arm. However, in other embodiments the patient positioning accessory support member may take other forms that are generally connected to the support frame. Arm 22 is connected to the support frame, and more particularly to the vertical column 12. The patient positioning arm 22 is movable relative to the support frame. More particularly, arm 22 can slide along the vertical column 12 so as to move up or down upon command through appropriate actuator(s) e.g. of the electric type. The patient positioning arm 22 extends from an arm support 22a that is slidably mounted relative to the fixed vertical part 12b. The patient positioning arm 22 extends along the apparatus in a direction that is substantially in correspondence with the direction of extension of horizontal mount 14. Here patient positioning arm 22 is arranged sideways relative to the apparatus in a substantial parallel relationship with horizontal mount 14.

Patient positioning accessory support member 22, here patient positioning arm 22, serves to position the patient in the apparatus at a given location.

Patient positioning arm 22 may include one of several patient positioning accessories generally located at a free end 22b of the arm or proximate thereto. With another patient positioning accessory support member, the accessory may be installed at any location that is not necessarily an end of the support member. These accessories may also or alternatively be considered as holding systems.

These patient positioning accessories allow to position the anatomical structures of the patient's head according to different orientations and to immobilize the patient's head during the examination so as to reduce any possible movement.

There exists one or several types of patient positioning accessories for each type of specific examination to be carried out by the apparatus according to different operating modes. The arm 22 is configured to accommodate each of these patient positioning accessories of different types, generally one at a time.

As illustrated in FIG. 1, one of these patient positioning accessories, noted 24, includes two temporal holding members that extend upwardly from the arm 22 to which they are removably attached. Only one temporal holding member is represented, the other one being hidden by the arm 16b.

Figure 2A:
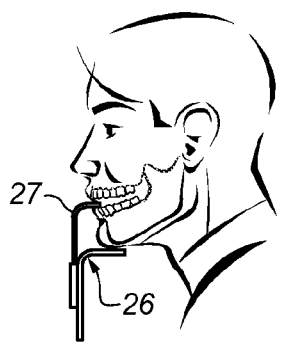
FIG. 2A-E show different possible patient positioning accessories.

The patient positioning accessory 24 also includes a chin rest 26 that extends upwardly from the arm 22 to which it is removably attached. The chin rest 26 is located between the two temporal holding members. The chin rest 26 equipped with a bit 27 is illustrated in FIG. 2A to position a patient's head for a panoramic examination.

Figure 2B:
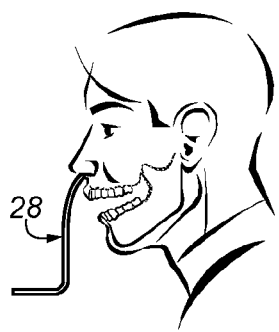
Figure 2C:
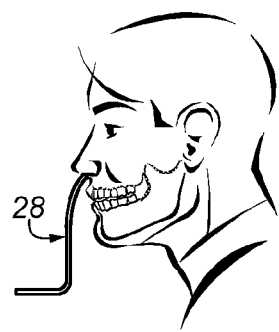
Figure 2D:
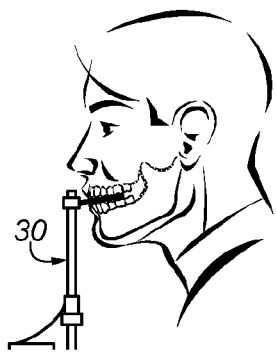

Other possible types of patient positioning accessories may be envisaged: a nasal support 28 for conducting a temporal mandible joint examination with open and closed mouth (see FIGS. 2B-C), a bitten support 30 (see FIG. 2D) for 3D examination (bit type), a frontal support 32 (see FIG. 2E including also temporal holding members 24) for 3D examination (frontal type), etc.

As illustrated in FIG. 1, a handle assembly 34 may be positioned at the free end 22b of the arm, underneath the arm and in a parallel relationship with the arm. This handle assembly 34 includes two vertical separate handle portions 34a, 34b which can be grasped by the patient when undergoing an imaging process so as to remain motionless.

Overall this handle assembly 34 has a U-shape which includes a horizontal base portion 34c and two vertical upwardly-extending branches 34a, 34b that are fixed to the arm 22. Each branch plays the role of a vertical handle portion.

Other assemblies may alternatively be used for handling the arm 22.

Patient positioning arm 22 may also support a monitor or display assembly 36 which makes it possible for a user of the apparatus to view and drive certain functions of the apparatus.

All that has been described above in relation with the patient positioning arm is applicable to any other patient positioning accessory support member.

Figure 3:
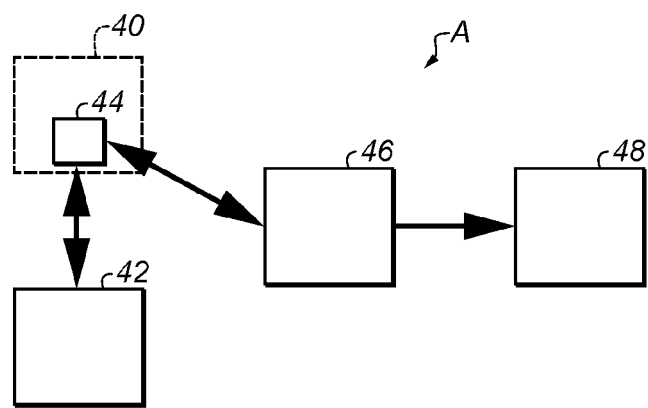
FIG. 3 is a schematic view of functional components of an apparatus according to an embodiment of the invention.

FIG. 3 is a schematic representation of functional components of an exemplary apparatus embodiment A according to the invention. The exemplary apparatus embodiment A may be that of FIG. 1 or any other extra oral dental imaging apparatus.

A patient positioning accessory 40 illustrated in dotted lines is mechanically mounted on the patient positioning accessory support member 42 (here member 42 is not necessarily an arm as in FIG. 1) and maintained thereon in a stable position.

According to certain exemplary method and/or apparatus embodiments herein, patient positioning accessory 40 comprises at least one passive identification element 44 that identifies the specific type of the patient positioning accessory. In other words element 44 is representative of the specific type of accessory. Thus different types of accessories are identified differently from each other thanks to the use of one or several passive identification elements. If the different types of accessories comprise only one passive identification element, then they can be distinguished from each other through different information contained in the element. Alternatively, several passive identification elements may be used for distinguishing different types of accessories: for example, different types of accessories may be uniquely identified each by a specific geometric configuration of a same number of passive identification elements or by different numbers of passive identification elements, possibly with varied geometric configurations.

The term "passive" means that the element has no reading or detecting function or any other active function. A passive element only carries or represents, e.g. by its shape or position, information which can be read or detected by another entity with an "active" function.

No electronic or electric function, e.g. no processor, no battery etc. are present in the passive element.

Further, the accessory itself does not contain any electronic or electric component.

According to certain exemplary method and/or apparatus embodiments herein, the exemplary apparatus embodiment A further comprises an active identification system 46 that may be in the patient positioning accessory support member 42 or not in any other part of the apparatus. Alternatively, system 46 may be separated from the apparatus, e.g. in a portable or stationary device. Active identification system 46 is complementary with the at least one passive identification element 44 in terms of functional cooperation or interaction. The two components 44 and 46 are configured by construction to cooperate or interact with each other so that the active component 46 be able to read or detect the identification information carried or represented by the passive component(s). This cooperation may be of the electromagnetic type, i.e. through detection of a magnetic field or transmission/reception of electromagnetic or optical waves between the two or several components. No contact is necessary between the components. This cooperation may alternatively be electromechanical or mechanical, i.e. the two or several components may mechanically engage with each other in a predetermined manner.

The purpose of the cooperation between active identification system 46 and the at least one passive identification element 44 is, for system 46, to identify the specific type of patient positioning accessory 40.

In the present exemplary embodiment, this identification is made while the patient positioning accessory 40 is supported by patient positioning accessory support member 42, such as accessory 24 mounted on arm 22 in FIG. 1. However, this identification may alternatively be made while the patient positioning accessory 40 is not supported by patient positioning accessory support member 42. This may be the case for instance when the two or several active and passive components electromagnetically cooperate with each other. The accessory may be presented for example in front of a reader or detector in the apparatus so as to read or detect the identification information carried or represented by the passive component(s).

The cooperation between active identification system 46 and the at least one passive identification element 44 leads to generation of one or more electric signals containing or representing identification information read or detected from the at least one passive identification element 44.

The active identification system 46 can further include a microprocessor for processing/analyzing the one or more electric signals resulting from the cooperation.

The processing step may lead to two results, alone or in combination, that are of interest to the physician:
(i) either the identification process shows that the identified accessory does correspond to the specific examination to be carried out on the apparatus, or
(ii) the identification process shows that the identified accessory is not the appropriate one relative to the specific examination.

The apparatus A may further comprise an information system 48 that is configured to generate information in relation with the specific type of the patient positioning accessory that has been identified. Appropriate information may be generated for each of results (i) and (ii) or for only one of them.

This information system may be a display assembly as 36 in FIG. 1 and appropriate information may be displayed thereon, e.g. through a visual indicator, so that the physician be visually informed accordingly.

Alternatively, or in a complementary manner, the information may be generated through a visual indicator on the accessory itself. For example, an appropriate source of light integrated in the support member 42 may illuminate the accessory. For better illumination results, the accessory may be made in a transparent or semi-transparent material.

Alternatively, the information may be audible and generated through a loudspeaker.

Figure 4:
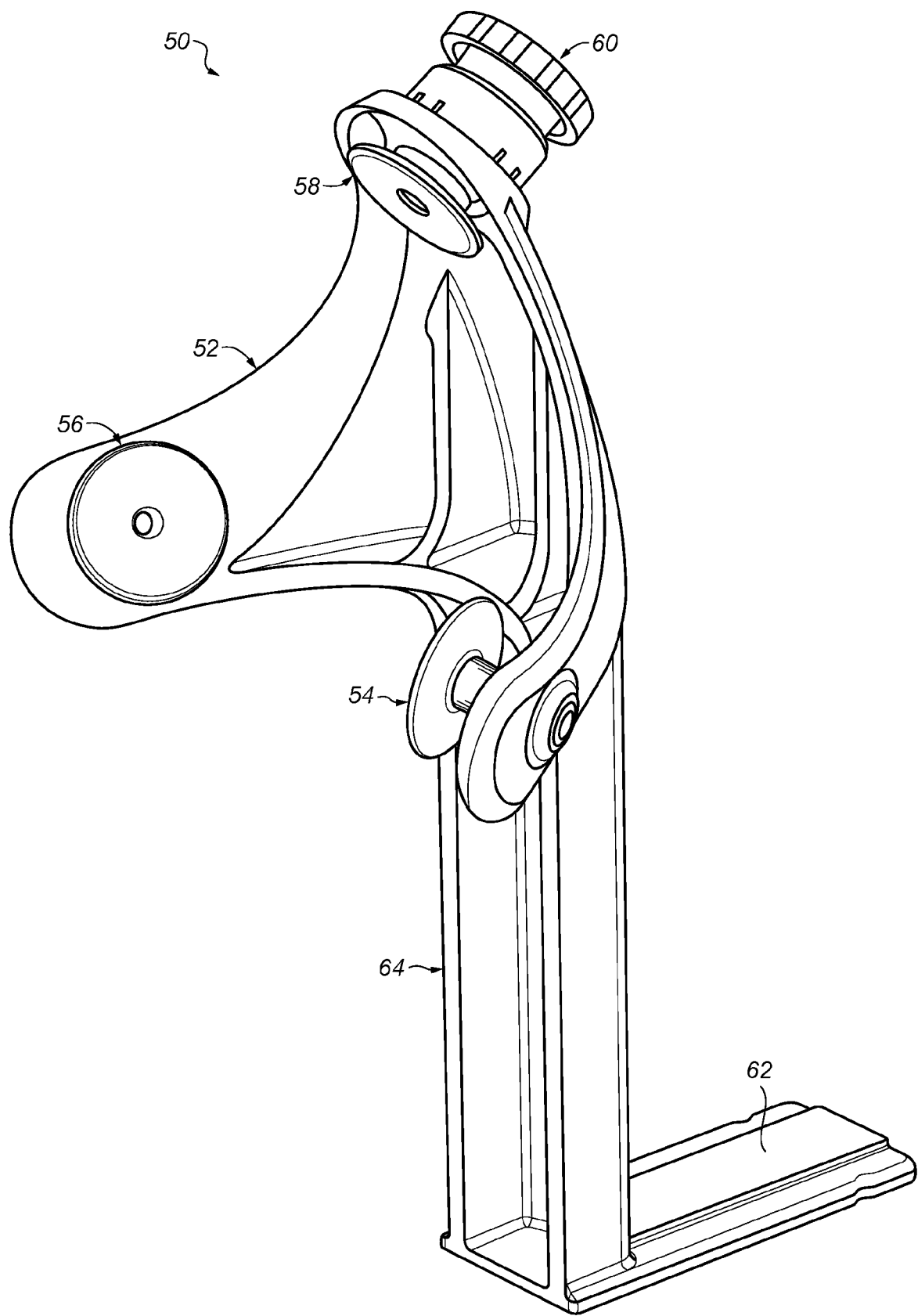
FIG. 4 is a view of an example embodiment of an accessory.

FIG. 4 is a perspective view of another example of a patient positioning accessory 50 which is a 3 points back of head support, here a 3 points support. It looks like a head restraint. Such an accessory may be used for a facial scan. The accessory comprises a head portion 52 that includes member(s)/equipment suitable for contacting and positioning the patient's head. Head portion is here a rigid frame, e.g. in the shape of a concave body, which partially surrounds the back of patient head. The frame 52 comprises two side surface supports 54, 56 which laterally maintain the head and an upper surface support 58 disposed between the two surface supports 54, 56 in a central part of the accessory. Upper surface support 58 is positioned rearward relative to the two surface supports 54, 56. Upper surface support 58 serves to manually adjust the head position through a screw member 60.

The head portion 52 is supported by a mounting support that has two portions: a base portion 62 intended to be removably installed/mounted on the patient positioning accessory support member 22 (see FIG. 8 for the accessory in position on the support member 22) and a connecting portion 64 that connects frame 52 to base portion 62.

In the present exemplary embodiment, the mounting support is substantially L shaped with an horizontal base portion 62 and a vertical connecting portion 64.

The head portion and the mounting support generally form an integral piece. Here, the connecting portion 64 has a structure configured to reinforce the mechanical strength of the mounting support. For example, the connecting portion has the shape of a gutter or of a metallic profile with a U shape with the inner side opposite the base portion. Here, the base portion 62 is substantially flat and is a base plate.

To be noted that all the accessories that have been previously described and illustrated have approximately the same structure: a head portion with member(s)/equipment suitable for contacting and positioning the patient's head (members/equipment differ overall between different accessories) and a mounting support with a base portion having the same structure for all the accessories. The connecting portion may differ between different accessories, e.g. in shape and/or height.

In other exemplary embodiments not depicted here, the base portion of the accessories that is removably installed/mounted on the patient positioning accessory support member (e.g. an arm of the apparatus) may take another shape.

Figure 5:
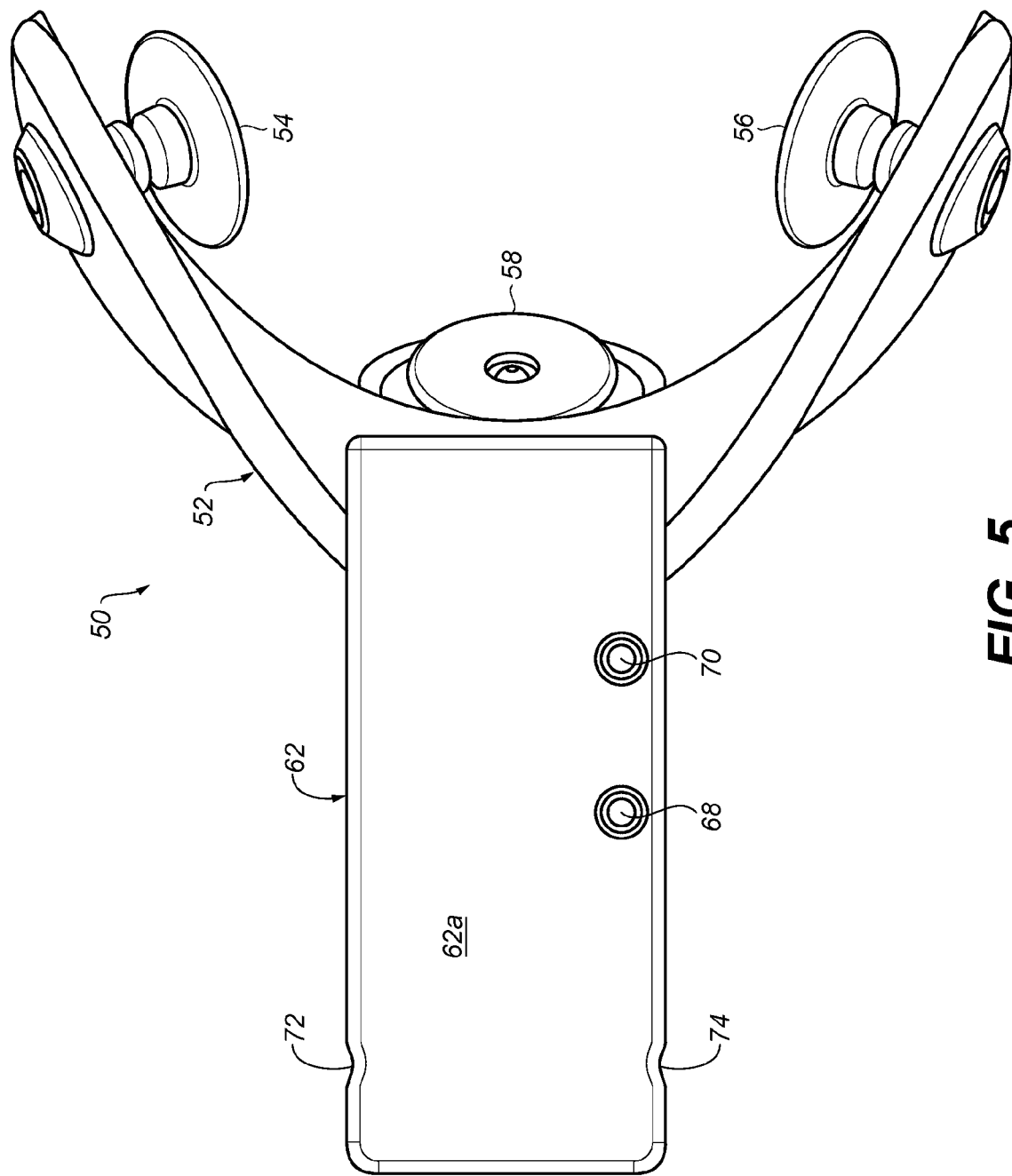
FIG. 5 shows a bottom view of the accessory of FIG. 4.

FIG. 5 is a bottom view of accessory 50 showing the base portion 62 and the head portion 52. Accessory 50 comprises here two identification passive elements 68, 70 that are mounted within base portion 62 in a given geometrical configuration. Elements 68, 70 may be flush mounted relative to the lower face 62*a* of base portion 62.

In the present exemplary embodiment elements 68, 70 are disposed along one longitudinal side of the base portion, in parallel with this side.

As represented, two notches 72, 74 are provided on the two opposite longitudinal sides of the base portion 62. These notches are intended to be engaged with appropriate protruding elements in the support member 22 so as to ensure the base portion is firmly positioned in the latter.

Figure 6:
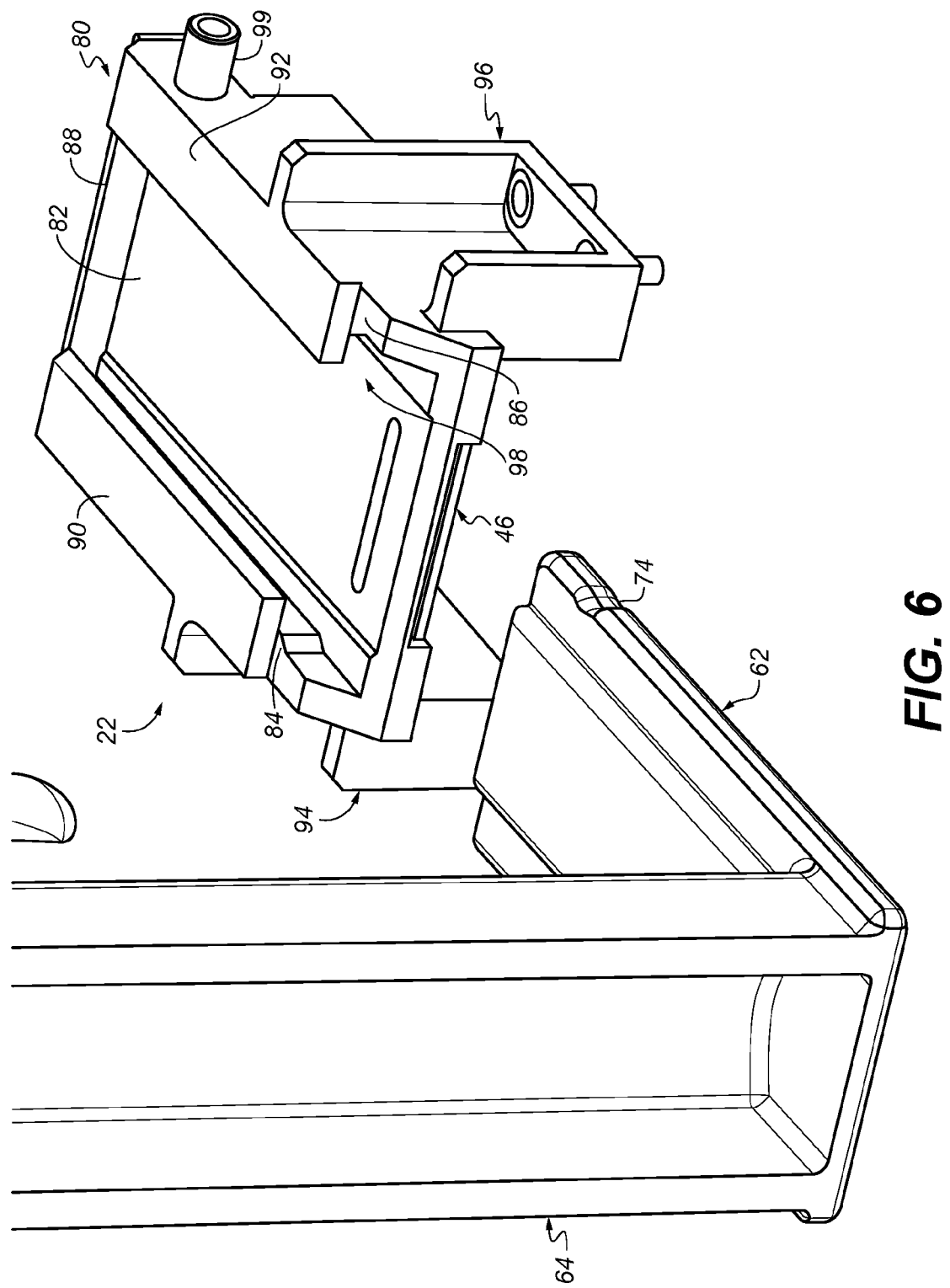
FIG. 6 shows a perspective partial view of the accessory of FIGS. 4 and 5 before installation in an accessory support member.

FIG. 6 illustrates a partial view of accessory 50 (only the mounting support) before installation in the patient positioning accessory support member 22. Here only a part of support member 22 has been represented: this part includes a receiving portion 80 for receiving the base portion 62 and the active identification system 46.

The receiving portion 80 can define a housing for accommodating base portion 62 therein. More particularly, the housing is formed by a lower plate 82 surrounded by three vertically-extending walls, two parallel longitudinal side walls 84, 86 and a rear wall 88, and two parallel upper longitudinal members 90, 92 that extend horizontally from the side walls partially above the lower plate so as to leave open the top of the housing. The housing is also open in its front face so as to define a slot 98 for inserting therein the base portion. The open front face is defined by an end of the lower plate 82, an end of the two side walls 84, 86 and an end of the two upper members 90, 92.

The receiving portion 80 is supported by leg portions 94, 96.

The active identification system 46 is disposed under lower plate 82 so as to be preferably protected by the latter.

Figure 7A:
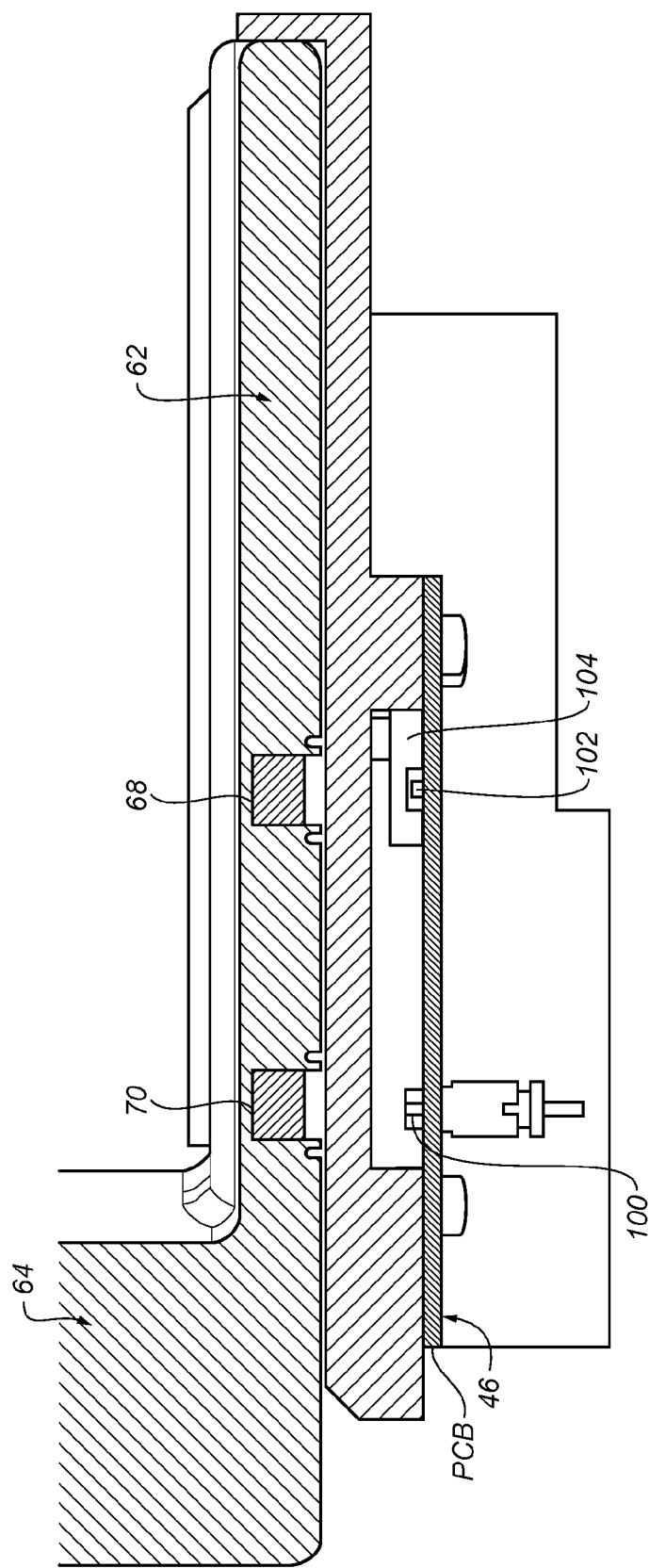
FIG. 7A is a cross section partial view of the accessory of FIGS. 4 and 5 installed in the accessory support member of FIG. 6.

As represented in FIG. 7A, the base portion 62 has been inserted into the slot 98 of the housing receiving portion 80. A prong member 99 appearing on FIG. 6 and traversing side wall 86 cooperates with notch 74 when base portion 62 is correctly engaged within the slot. A corresponding prong (not visible) located on the other facing side wall 84 is also provided to cooperate likewise with the other notch 76 (not represented in FIG. 6).

In a general manner, the exemplary active identification system 46 according to some embodiments as shown in FIG. 3 comprises:

one or several detection elements that are configured to cooperate with the at least one passive identification element of the patient positioning accessory and generate at least one signal depending on the result of the cooperation, and a microprocessor configured to analyze the at least one signal thus generated in order to identify the specific type of the patient positioning accessory.

In the present exemplary embodiment, the active identification system 46 comprises a printed circuit board PCB (FIG. 7A) that carries for example four detection elements which are here magnetic sensors such as Hall effect sensors, and which may be disposed on the PCB in a square or rectangular arrangement. Only two detection elements 100, 102 are visible in this drawing, the other two being not in this cross section.

Figure 7B:
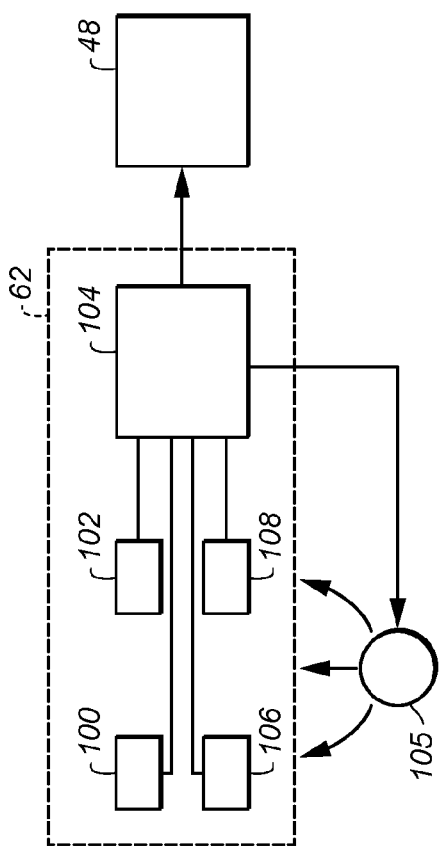
FIG. 7B is a schematic view of components of the active identification system according to one embodiment.

The PCB also carries a microprocessor 104 that is connected to the detection elements 100, 102, 106 and 108 as represented in top view on FIG. 7B.

The accessory 50 is uniquely identified by the presence and geometric arrangement of the two magnets 68 and 70 in base portion 62.

Another type of accessory is uniquely identified by another number and/or geometric arrangement of magnets.

Here the two magnets 68 and 70 are in such a position that only the two detection elements 100, 102 which are in register with the magnets (the magnets 68, 70 are respectively located above detection elements 102, 100) are able to detect their presence. The two Hall effect sensors 100, 102 detect the magnetic fields generated by the magnets 70, 68 respectively while the other two not represented Hall effect sensors do not detect any magnetic field. These sensors generate electric signals that are representative of the presence of absence of magnets in the base portion, and therefore identify (or represent identification information) the type of accessory.

The microprocessor 104 receives and analyzes the electric signals generated by the four sensors so as to identify the type of accessory. The microprocessor 104 may be configured to directly compare the identified type of accessory with that required for conducting a specific examination (operating mode) with the apparatus.

This comparison step may then lead to decide that the identified type of accessory is the correct one for the specific examination to conduct or that it is an incorrect one.

Next a corresponding signal result S is sent by the microprocessor to the information system 48. Corresponding information is then generated for informing the user of the apparatus as already mentioned above.

Alternatively, once the microprocessor has identified the type of accessory, a signal containing such an information or representative of the latter is generated and sent to information system 48 or any other computer system in the apparatus. Either information system 48 or the other computer system then proceeds to this comparison and decision steps.

Figure 8:
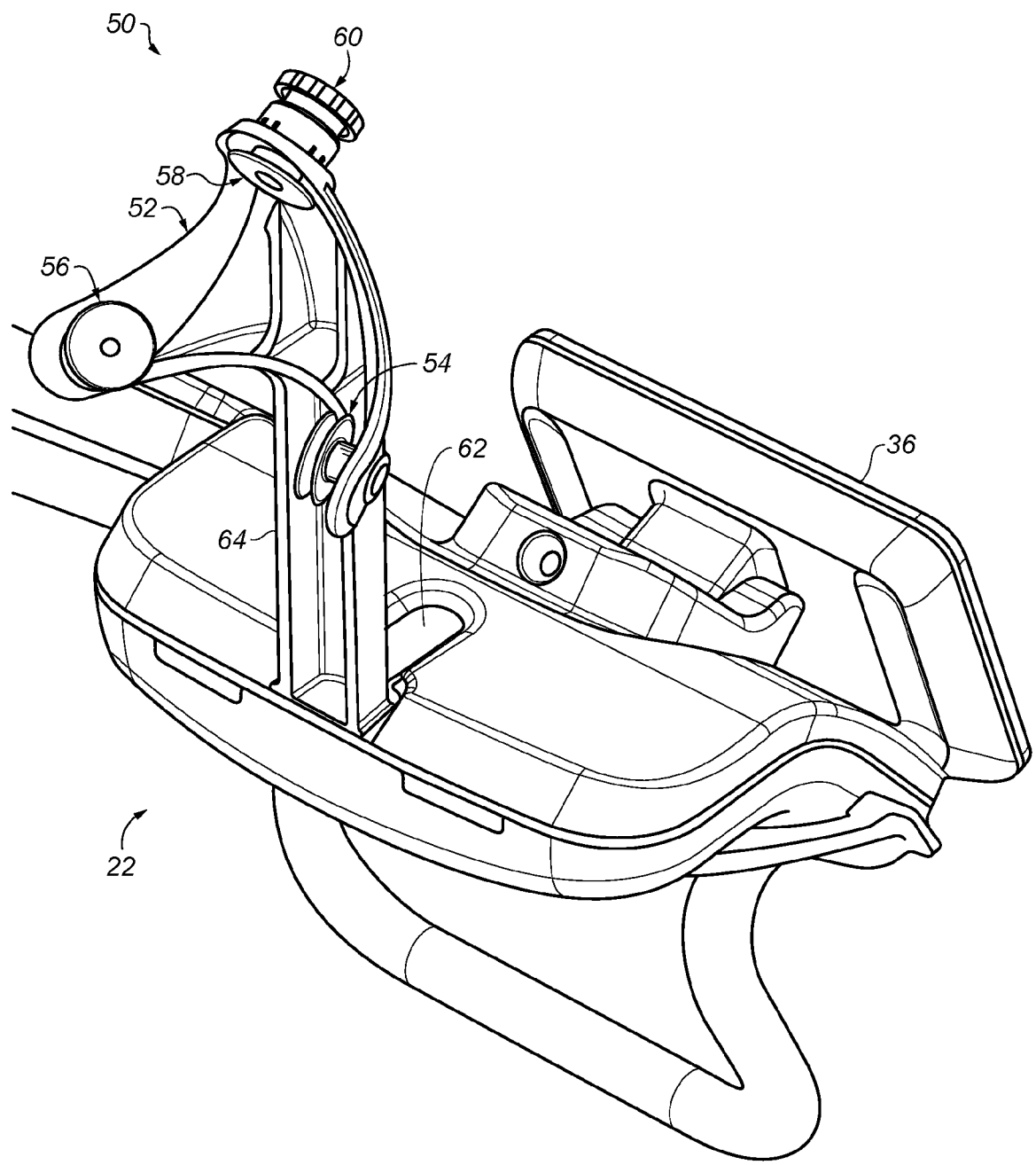
FIG. 8 is a perspective view of the accessory of FIGS. 4 and 5 installed in the accessory support member.

As represented in FIG. 8, when the accessory is positioned in the accessory support member 22, the base portion 62 is visible from the above due to the open housing of FIG. 6. Base portion 62 and possibly connecting portion 64 may be made in a transparent material such as polycarbonate and may be illuminated by light source(s) placed under the base portion or sideways when the latter is installed in the accessory support member.

In FIG. 7B light source (ex: LED source) 105 may be placed laterally relative to base portion 62 and is commanded by microprocessor 104 (or another entity) to illuminate the latter. Thus light may be scattered through the base portion, and possibly the connecting portion, which is apparent from the above for a user (see FIG. 8).

Several light sources (ex: several LEDs of different colors) may be used for illuminating differently the base portion according to the accessory that has been identified. The user of the apparatus is therefore informed accordingly and can take the appropriate steps, e.g., either conducting the examination with the correct identified accessory or changing the accessory before conducting the examination.

Figure 7C:
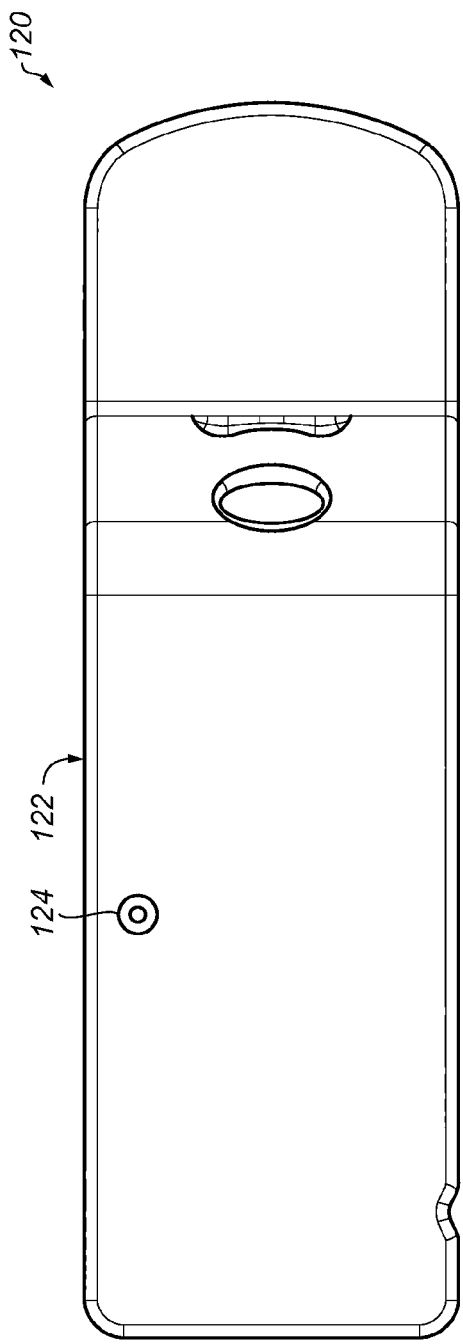
FIGS. 7C and 7D show a bottom view of two other types of accessory respectively.

Another exemplary accessory embodiment 120 is illustrated on FIG. 7C and shows a bottom view thereof. The base portion 122 comprises one magnet 124 which is here positioned differently from the magnets of FIG. 5: magnet 124 is disposed in the bottom left corner of a square or rectangle whereas the magnets 68 and 70 of FIG. 5 are disposes on the right side of the square or rectangle at the two adjacent corners. Magnet 124 will therefore be detected by the magnetic sensor disposed in geometric correspondence on the PCB.

Accessory 120 is a chin rest accessory as illustrated in FIG. 2A.

Figure 7D:
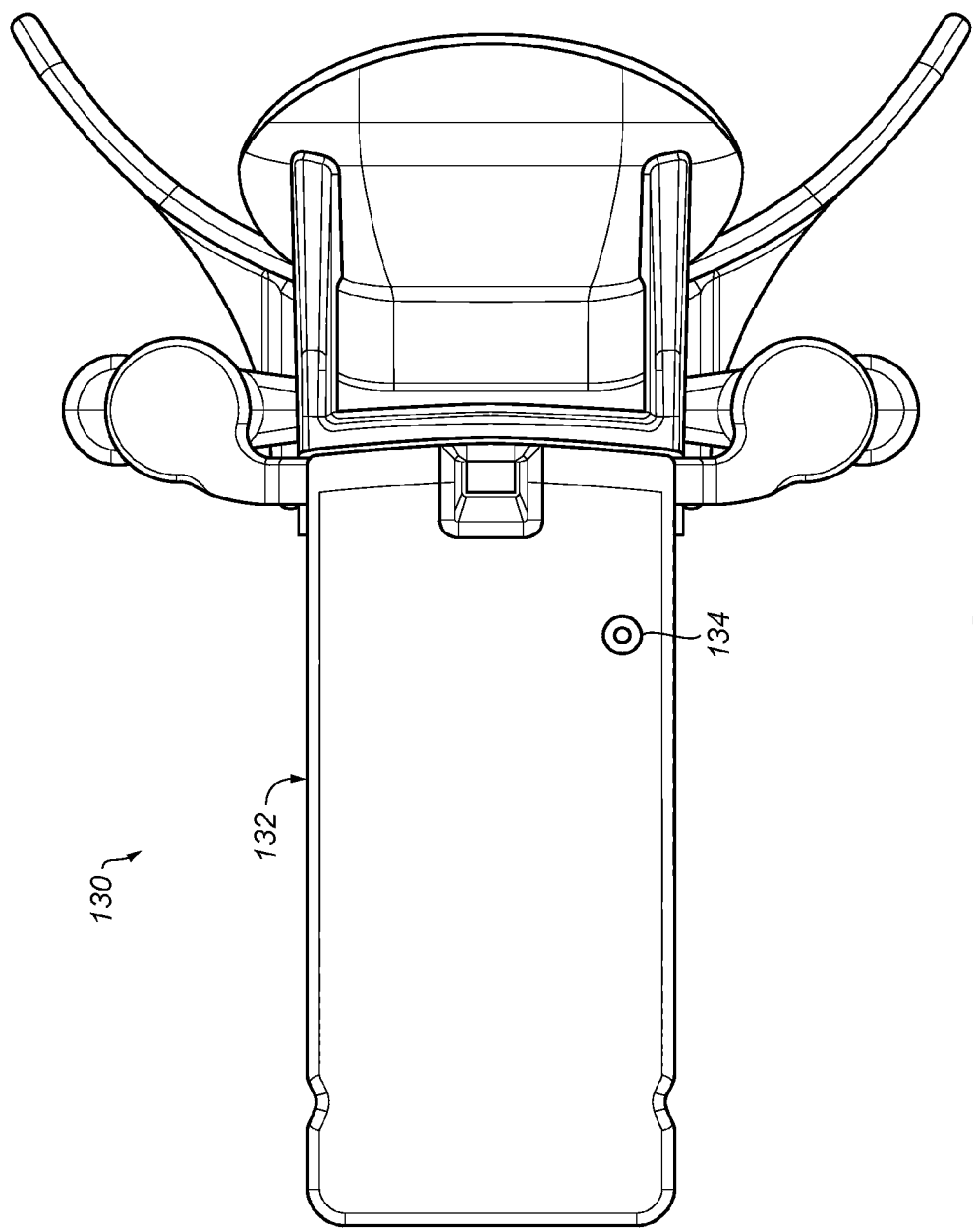

Yet another exemplary accessory embodiment 130 is illustrated on FIG. 7D and shows a bottom view thereof. The base portion 132 comprises one magnet 134 arranged differently from the magnet 124 of FIG. 7C, here in the upper right corner of the above-mentioned square or rectangle. Magnet 134 will therefore be detected by the magnetic sensor disposed in geometric correspondence on the PCB.

Figure 2E:
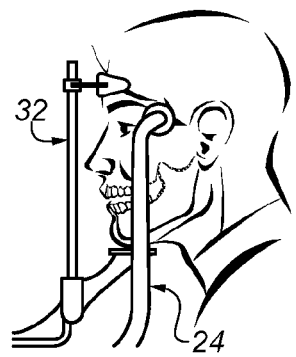

Accessory 130 is a frontal support as illustrated on FIG. 2E.

In a general manner, the passive identification element(s) in the patient positioning accessory, more particularly in the base portion thereof, may be embedded in the material constituting the base portion or overmolded. The identification element(s) being of the passive type as explained above, this makes it possible for the accessory to be placed in an autoclave for sterilization purpose. An identification element of an active type, e.g. with a microprocessor and/or a battery, could not withstand temperatures used in an autoclave (ex: 120-140° C.).

Other variant exemplary embodiments will now be described with reference to FIGS. 9A to 9L.

Figure 9A:
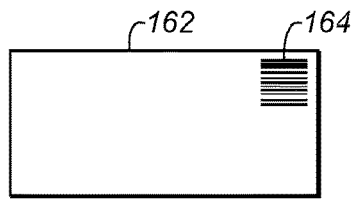
FIGS. 9A-L show different variant embodiments of active and passive components.
Figure 9B:
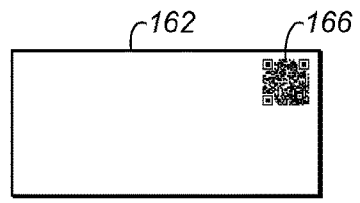

FIGS. 9A and 9B illustrate other types of exemplary passive identification elements carried by an accessory, here its base portion 162. For example, a bar code 164 or a QR code 166 may be positioned on the lower face of the base portion that may be disposed facing the base plate 98 of FIG. 6 or any other element of the accessory support member.

Figure 9C:
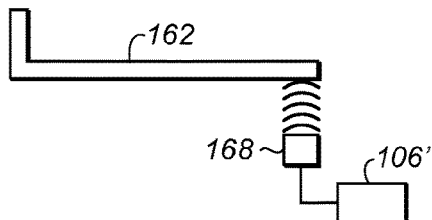

As represented in FIG. 9C, a bar code or QR code reader 168 is placed under the base portion, e.g. on a printed circuit board such as PCB in FIG. 7A, and reads the corresponding identification code (identification information) on the base portion.

The present PCB also includes a microprocessor 104' connected to the code reader 168 and that receives the resulting signal from the code reader 168.

As for the above described exemplary embodiment the identification information read from the accessory's base portion is compared with the identification information of the requested type of accessory for the specific examination to conduct (e.g., stored in a database) and decision is taken as to the identification of the accessory in the accessory support member. Then the information system 48 generates appropriate information to warn the apparatus user (ex: physician) of the identification process.

Different accessories bear different optical codes and are therefore uniquely identifiable by the optical reader.

All that has been described above also applies here and will not be repeated.

Figure 9D:
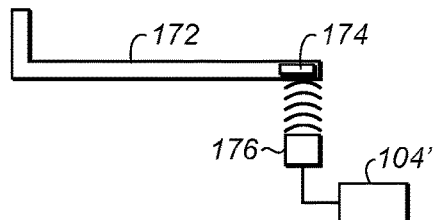

As another exemplary variant embodiment illustrated in FIG. 9D, the accessory's base portion 172 includes an RFID tag 174 that bears identification information specific to the type of accessory. Tag 174 may be encapsulated in the body of the base portion.

All the base portions of the different types of accessories are identical ad differ only through the information each RFID tag contain. This information may be inscribed in the tag when programming the latter before its use.

An RFID reader 176 placed underneath when the base portion is in its working position in the accessory support member reads the identification information contained in the tag 174. RFID reader which may be on a PCB sends its electric signal containing or representative of the read information to the microprocessor 104' on the PCB.

The following steps are identical to what has already been explained above with reference to FIGS. 9A-C and will not be repeated here.

FIGS. 9E to 9H still illustrate other optical variant exemplary embodiments involving optical source/detectors and holes or marks in the base portion of an accessory. The optical source/detectors are connected to a microprocessor not represented here but similar of microprocessors 104 and 104' described above.

Figure 9E:
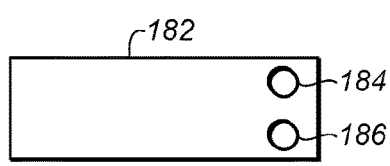
Figure 9F:
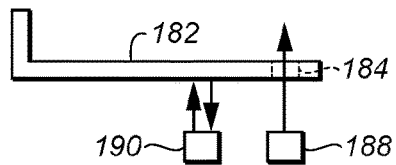

FIG. 9E shows a base portion 182 with a plurality of through holes 184, 186 traversing the base portion in its thickness or height (see FIG. 9F).

When the base portion 182 is installed within its housing in the accessory support member (FIG. 9F) optical source/detectors, two of which only being represented 188, 190, are able to interact with the base portion and to detect the presence of holes or their absence according to the corresponding positions of the holes and the optical source/detectors. In the present exemplary embodiment, optical source/detector 188 emits optical radiation through hole 184 and does not receive any reflected radiation while optical source/detector 190 both emits and receives optical radiation.

Other optical source/detectors (not represented) are disposed in other locations on a PCB in register with possible locations of holes so as to detect their presence if any.

In the present exemplary embodiment, the two holes 184 and 186 have been detected and the absence of other possible holes has also been detected. Such a detection is representative of a specific type of accessory, as a unique code.

Other possible codes identify other specific types of accessories. For example, a base portion with a single hole identifies another type of accessory.

All that has been described above also applies here and will not be repeated.

Figure 9G:
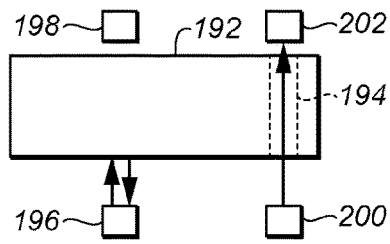

In FIG. 9G a base portion 192 is pierced in its width by one long hole 194 and two pairs of optical emitters and receivers 196, 198 and 200, 202 are located on either side of the base portion. This arrangement or configuration is such that optical radiation emitted by an emitter of a pair is received or not by a corresponding receiver of the pair according to the presence of absence of a traversing hole.

This also enables coding, and therefore identification, of the accessory.

Figure 9H:
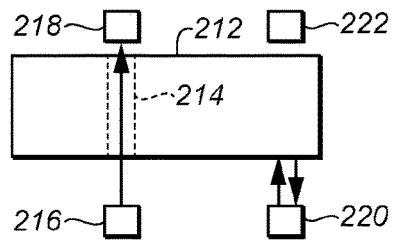

FIG. 9H illustrates another arrangement identifying another exemplary accessory embodiment with a base portion 212 pierced by a long hole 214 and two pairs of optical emitters and receivers 216, 218 and 220 and 222.

All that has been described above also applies here and will not be repeated.

FIGS. 9I to 9L illustrate other variant exemplary embodiments which involve mechanical cooperation between the passive identification element(s) and the active identification system.

Figure 9I:
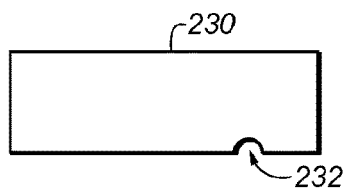

In FIG. 9I an accessory base portion 230 includes a recess 232 formed on the outline of the base portion on a side thereof.

The active identification system includes several detection elements 234-240 positioned on the two longitudinal sides of the base portion 230 when the latter has been installed in the housing of the accessory support member.

Each detection element may comprise a prong member mounted on an elastic member, e.g. a spring, and that occupies two positions, an extended and a folded position, according to the presence or absence of a recess in register therewith in the base portion. For example, in the folded position an electric contact is established in a circuit by the detection element whereas no electric contact is established in the extended position.

Figure 9J:
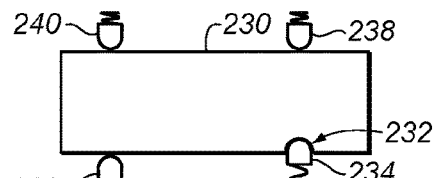

In FIG. 9J the prong member 234 is in an extended position since the recess 232 is in register therewith whereas the other three prong members 236, 238 and 240 are in a folded position since no other recesses are present in the base portion.

This arrangement or configuration of the detection elements 234-240 generates an electric signal that is sent to a microprocessor not represented here but similar to the above-described microprocessors 104 and 104'. The generated electric signal is generated following both the establishment of electric contacts through detectors 236, 238 and 240 and the non-establishment of an electric contact with detector 234.

This generated electric signal is therefore representative of the outline of the base portion (i.e. the presence of a single recess), which corresponds to an identification code, that will provide identification of the accessory as already explained above.

All that has been described above also applies here and will not be repeated.

Figure 9K:
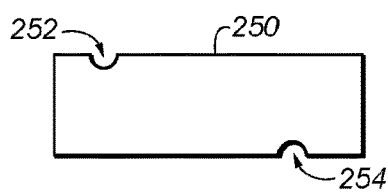
Figure 9L:
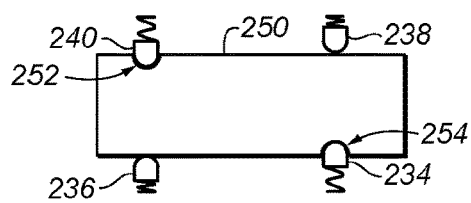

In FIGS. 9K and 9L, the base portion 250 has two recesses 252 and 254 which are detected by the detectors 234-240 as described above. Here both detectors 234 and 240 are in an extended position, while the other two stay in a folded position, which leads to a different identification code of another type of accessory.

To be noted that the detection elements are here local position indicators (e.g., of the mechanical type). In other variant exemplary embodiments, the local position indicators may be different in shape and located in a different place relative to an accessory base portion, e.g. under the base portion. In a general manner, the identification of an accessory is based on the position of movable indicator(s) relative to the accessory's base portion.

Different types of mechanical assemblies may be used for mechanically coding or identifying an accessory type and detecting the latter. Different mortises and tenon joints may be used etc.

It is to be noted that in all the exemplary method and/or apparatus embodiments that have been described above the number, shapes, types, positions of the different components (either active or passive) may vary. In particular, the base portion of the accessories may differ in shape and type and may cooperate differently with the patient positioning accessory support member, e.g., an arm or any other type of support member.

Also with other types of accessories, the passive element(s) may be placed in another location on the accessory.

Certain exemplary method and/or apparatus embodiments herein can also be configured to receive patient positioning accessories of other types for conducting x-ray examination on other parts of a patient than the head or maxillofacial region. For example, a wrist patient positioning accessory may be used in the apparatus for conducting x-ray examination on the wrist of a patient and therefore obtaining a radiographic image thereof. All that has been described above also applies here and will not be repeated.

The invention may also concern a computer program product which may include one or more storage medium, for example; magnetic storage media such as magnetic disk (such as a floppy disk) or magnetic tape; optical storage media such as optical disk, optical tape, or machine readable bar code; solid-state electronic storage devices such as random access memory (RAM), or read-only memory (ROM); or any other physical device or media employed to store a computer program having instructions for controlling one or more computers to practice exemplary method and/or apparatus embodiments described herein. The computer program may be stored in a memory on the above described PCB, in another location of the active identification system, in the information system or in any other location in the apparatus or even in a separate location.

Consistent with exemplary embodiments herein, a computer program can use stored instructions that perform on image data that is accessed from an electronic memory. As can be appreciated by those skilled in the image processing arts, a computer program for operating the imaging system and probe and acquiring image data in exemplary embodiments of the application can be utilized by a suitable, general-purpose computer system operating as described herein, such as a personal computer or workstation. However, many other types of computer systems can be used to execute the computer program of the present invention, including an arrangement of networked processors, for example. The computer program for performing exemplary method embodiments may be stored in a computer readable storage medium. This medium may include, for example; magnetic storage media such as a magnetic disk such as a hard drive or removable device or magnetic tape; optical storage media such as an optical disc, optical tape, or machine readable optical encoding; solid state electronic storage devices such as random access memory (RAM), or read only memory (ROM); or any other physical device or medium employed to store a computer program. Computer programs for performing exemplary method embodiments may also be stored on computer readable storage medium that is connected to the image processor by way of the internet or other network or communication medium. Those skilled in the art will further readily recognize that the equivalent of such a computer program product may also be constructed in hardware.

It should be noted that the term "memory", equivalent to "computer-accessible memory" in the context of the application, can refer to any type of temporary or more enduring data storage workspace used for storing and operating upon image data and accessible to a computer system, including a database, for example. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Display data, for example, is typically stored in a temporary storage buffer that is directly associated with a display device and is periodically refreshed as needed in order to provide displayed data. This temporary storage buffer is also considered to be a type of memory, as the term is used in the application. Memory is also used as the data workspace for executing and storing intermediate and final results of calculations and other processing. Computer-accessible memory can be volatile, non-volatile, or a hybrid combination of volatile and non-volatile types.

It will be understood that computer program products of the application may make use of various image manipulation algorithms and processes that are well known. It will be further understood that computer program product exemplary embodiments of the application may embody algorithms and processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with the computer program product exemplary embodiments of the application, are not specifically shown or described herein and may be selected from such algorithms, systems, hardware, components and elements known in the art.

Exemplary embodiments according to the application can include various features described herein (individually or in combination).

While the invention has been illustrated with respect to one or more implementations, alterations and/or modifications can be made to the illustrated examples without departing from the spirit and scope of the appended claims. In addition, while a particular feature of the invention can have been disclosed with respect to only one of several implementations/embodiments, such feature can be combined with one or more other features of the other implementations/embodiments as can be desired and advantageous for any given or particular function. The term "at least one of" is used to mean one or more of the listed items can be selected. The term "about" indicates that the value listed can be somewhat altered, as long as the alteration does not result in nonconformance of the process or structure to the illustrated embodiment. Finally, "exemplary" indicates the description is used as an example, rather than implying that it is an ideal. Other embodiments of the invention will be apparent to those skilled in the art from consideration of the specification and practice of the invention disclosed herein. It is intended that the specification and examples be considered as exemplary only, with a true scope and spirit of the invention being indicated by at least the following claims.

What is claimed is:

1. An extra oral dental imaging apparatus for obtaining a radiographic image of a patient, the apparatus comprising:
    a support frame;
    a movable gantry that supports an x-ray source and an x-ray sensor in correspondence with the x-ray source and that is movable relative to the support frame; and
    a patient positioning accessory support member configured to support a patient positioning accessory of a specific type of a plurality of different patient positioning accessories that is adapted to be used in the apparatus for conducting a specific examination of a plurality of different examinations on a patient;
    wherein the patient positioning accessory comprises at least one passive identification element that identifies the specific type of the patient positioning accessory; and
    wherein the apparatus further comprises an active identification system that is configured to cooperate with the at least one passive identification element of the patient positioning accessory in order to identify the specific type of the patient positioning accessory and to determine, based on the identified specific type, whether the patient positioning accessory is or is not the appropriate type for the specific examination on a patient.

2. The dental imaging apparatus of claim 1, wherein the apparatus further comprises an information system configured to generate information in relation with the specific type of the patient positioning accessory that has been identified.

3. The dental imaging apparatus of claim 2, wherein the information system comprises a display assembly configured to display information in relation with the specific type of the patient positioning accessory that has been identified.

4. The dental imaging apparatus of claim 3, wherein the apparatus is further configured to generate a visual indicator on the display assembly or on the patient positioning accessory, the visual indicator being in relation with the specific type of the patient positioning accessory that has been identified.

5. The dental imaging apparatus of claim 1, wherein the active identification system is in the patient positioning accessory support member.

6. The dental imaging apparatus of claim 1, wherein the patient positioning accessory support member is a patient positioning arm connected to the support frame.

7. The dental imaging apparatus of claim 1, wherein the active identification system comprises:
   one or several detection elements that are configured to cooperate with the at least one passive identification element of the patient positioning accessory and generate at least one signal depending on the result of the cooperation, and
   a microprocessor configured to analyze the at least one signal thus generated in order to identify the specific type of the patient positioning accessory.

8. The dental imaging apparatus of claim 7, wherein the one or several detection elements are selected among magnetic sensors, optical sensors, optical readers, at least one local position indicator.

9. The dental imaging apparatus of claim 7, wherein the at least one passive identification element of the patient positioning accessory is selected among a magnet, a mark or hole in the patient positioning accessory, an optical code on the patient positioning accessory, an RFID tag, a concavity in the outline of the patient positioning accessory.

10. The dental imaging apparatus of claim 1, wherein the active identification system is configured to mechanically or electromagnetically cooperate with the at least one passive identification element of the patient positioning accessory.

11. The dental imaging apparatus of claim 1, wherein the apparatus further comprises further comprises:
   a second patient positioning accessory of a second specific type that is adapted to be supported by the patient positioning accessory support member when used in the apparatus for conducting a second specific examination of the plurality of different examinations on the patient;
   wherein the second patient positioning accessory comprises at least one passive identification element that identifies the second specific type of the patient positioning accessory; and
   wherein the active identification system is configured to cooperate with the at least one passive identification element of the second patient positioning accessory in order to identify the second specific type of the patient positioning accessory and to determine, based on the identified second specific type, whether the second patient positioning accessory is or is not the appropriate type for the second specific examination when supported by the patient positioning accessory support member.

12. The dental imaging apparatus of claim 11, wherein the plurality of different examinations comprises panoramic examinations, computed tomographic (CT) examinations, or cephalometric examinations.

13. A method for using an extra oral dental imaging apparatus for obtaining a radiographic image of a patient, the apparatus comprising:
   a support frame;
   a movable gantry that supports an x-ray source and an x-ray sensor in correspondence with the x-ray source and that is movable relative to the support frame, wherein the apparatus is adapted to perform a plurality of different examination types using the support frame and the moveable gantry;
   a patient positioning accessory support member configured to support a patient positioning accessory of a specific type of a plurality of different patient positioning accessory types that is adapted to be used in the apparatus for conducting a specific examination type of the plurality of different examination types on a patient;
   wherein the method comprises the steps of:
      installing the patient positioning accessory of the specific type on the patient positioning accessory support member,
      identifying the specific type of the patient positioning accessory based on at least one passive identification element included in the patient positioning accessory, and
      determining, based on the identified specific type, whether the patient positioning accessory is or is not of the appropriate type for conducting the specific examination type on the patient.

14. The method of claim 13, wherein the apparatus further comprises an active identification system and the method further comprises a step of causing cooperation between the active identification system and the at least one passive identification element of the patient positioning accessory in order to identify the specific type of the patient positioning accessory.

15. A computer storage product having at least one computer storage medium having instructions stored therein causing one or more computers to perform the method of claim 13.

16. The method of claim 13, wherein the method further comprises the steps of:
   replacing the patient positioning accessory of the specific type with a second patient positioning accessory of a second specific type of the plurality of different patient positioning accessory types on the patient positioning accessory support member,
   identifying the second specific type of the patient positioning accessory based on at least one passive identification element included in the second patient positioning accessory, and
   determining, based on the identified second specific type, whether the patient positioning accessory is or is not of the appropriate type for conducting the second specific examination type on the patient.

* * * * *